(12) United States Patent
Bilbeny Lojo et al.

(10) Patent No.: US 7,026,514 B2
(45) Date of Patent: Apr. 11, 2006

(54) COMPOUNDS USED TO TREAT ALCOHOLISM

(75) Inventors: Norberto Bilbeny Lojo, Santiago de Chile (CL); Hernan Garcia Madrid, Santiago de Chile (CL); Maria Belen Font Arellano, Pamplona (ES)

(73) Assignee: Garbil Pharma Investigacion Chile Ltda., Santiago de Chile (CL)

( * ) Notice: Subject to any disclaimer, the term of this patent is extended or adjusted under 35 U.S.C. 154(b) by 0 days.

(21) Appl. No.: 10/482,708

(22) PCT Filed: Jul. 1, 2002

(86) PCT No.: PCT/ES02/00323

§ 371 (c)(1), (2), (4) Date: Jan. 5, 2004

(87) PCT Pub. No.: WO03/004453

PCT Pub. Date: Jan. 16, 2003

(65) Prior Publication Data

US 2004/0180967 A1    Sep. 16, 2004

(30) Foreign Application Priority Data

Jul. 5, 2001    (ES)    ................ 200101642

(51) Int. Cl.
C07C 211/36    (2006.01)
C07C 233/08    (2006.01)
A61K 31/132    (2006.01)
A61P 25/32    (2006.01)

(52) U.S. Cl. .............. 564/461; 564/448; 564/454; 564/462; 514/659

(58) Field of Classification Search ............. 564/448, 564/454, 461; 514/659
See application file for complete search history.

(56) References Cited

U.S. PATENT DOCUMENTS 5,534,553 A    7/1996    Hoerrmann
5,962,533 A    10/1999    Bergeron
6,399,662 B1    6/2002    Bergeron

OTHER PUBLICATIONS

Klenke et al., J. Org. Chem. 2001, 66(7), p. 2480-2483.*
Protective Groups in Organic Synthesis, 3rd ed., editors, Theodora W. Greene and Peter G. M. Wuts, 1999, John Wiley & Sons, Inc., New York, pp. 492-495, 518 (e-book).*
Jerry March, *Advanced Organic Chemistry*, Jhon Wiley & Sons, Wiley Interscience, 4th Edition, ISBN 0-471-60180-2, pp. 918-919, reaction (Jun. 27, 1992).

* cited by examiner

*Primary Examiner*—Brian Davis
(74) *Attorney, Agent, or Firm*—Sughrue Mion, PLLC

(57) ABSTRACT

N,N'-bis(3-aminopropyl)cyclohexane-1,4-diamine, of formula (I), is a new compound that is prepared by hydrogenation with Raney nickel catalyst of N,N'-bis(2-cyanoethyl)-cyclohexane-1,4-diamine, the latter being prepared by reaction between 1,4-cyclohexanediamine and acrylonitrile. The oral administration to genetically alcoholic rats (from the strain UChB of the University of Chile) of the tetrametanesulfonate monohydrate of (I) causes a significant reduction in the alcohol consumption. The activity lasts for some time after the treatment period. Besides, there is a virtually null disulfiram-like adverse effect, what constitutes an advantage over the unpleasant use of some anti-alcoholism agents, such as calcium cyanamide or disulfiram itself. Therefore, the compounds of the invention are useful for the preparation of medicaments for the therapeutic and/or prophylactic treatment of alcoholism in mammals, including human beings

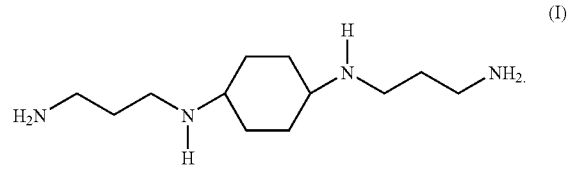

(I)

17 Claims, No Drawings

COMPOUNDS USED TO TREAT ALCOHOLISM

This Application is a 371 of PCT/ES02/00323, filed Jul. 1, 2002; the disclosure of which is incorporated herein by reference.

This invention relates to new compounds, their preparation process and their use for preparing compositions for the treatment of alcoholism in mammals, including human beings.

BACKGROUND ART

The expression "treatment of alcoholism" comprises the reduction of the desire for and habit of consuming alcoholic drinks, the treatment of alcohol dependence and the treatment of abstinence syndrome. Alcoholism may be viewed as a disease, a drug addiction, a learned response to crisis, a symptom of an underlying psychological or physical disorder, or a combination of these factors. Most approaches to the treatment of alcoholism require the alcoholic person to recognize his/her illness and to abstain from alcohol. Treatment programs then vary according to the accepted definition and theory of cause of alcoholism. Treatment types include combinations of: psychological rehabilitative treatments; organized self-help groups; aversion therapy based on behavior modification; injections of vitamins or hormones, and the use of abstinence-maintaining drugs. The present invention relates to the latter type of treatments.

One of the drug treatments of alcoholism, initiated in 1948 by Eric Jacobsen of Denmark, uses disulfiram (tetraethylthiuram disulfide), of formula $Et_2N-C(=S)-S-S-C(=S)-NEt_2$. The usual technique is to administer half a gram in tablet form daily for a few days; then, under carefully controlled conditions and with medical supervision, the patient is given a small drink of an alcoholic beverage. The presence of disulfiram in the drinker's body causes a reaction of hot flushing, nausea, vomiting, a sudden sharp drop of blood pressure, pounding of the heart, and even a feeling of impending death. These symptoms, usually known as 'acetaldehyde syndrome' or 'disulfiram-like adverse effect', result from an accumulation of the highly toxic first product of alcohol metabolism, acetaldehyde. Normally, as alcohol is converted to acetaldehyde, the latter is rapidly converted, in turn, to other harmless metabolites; but in the presence of disulfiram—itself non-toxic, although not completely innocuous—the metabolism of acetaldehyde is blocked, with the resulting toxic symptoms. The patient is thus dramatically shown the danger of attempting to drink while under disulfiram medication. A smaller daily dose of disulfiram is then prescribed, and the dread of the consequences of drinking acts as a chemical fence to prevent the patient from drinking as long as he continues taking the drug.

Besides being quite unpleasant for patients, treatment of alcoholism with disulfiram involves a high risk, because subjects treated with disulfiram suffer from very serious symptoms deriving from the ingestion of even small doses of alcohol. Thus, following disulfiram treatment cases of respiratory depression, cardiovascular collapse, cardiac arrhythmia, myocardium infarct, and sudden or unexpected death have occurred.

Citrated calcium cyanamide (two parts of citric acid by weight to one part of CaNCN) is another drug used as anti-alcoholism agent, which has a disulfiram-like mechanism of action. It is preferred by some therapists because the reaction with alcohol is milder than in the case of disulfiram, though its protective potency is briefer. Other substances that can produce disagreeable reactions with alcohol include animal charcoal, the mushroom *Coprinus atramentarius*, numerous antidiabetic drugs, and the pine *Lycopodium selago*; however they have attracted very little clinical interest. Thus, in the last years, there have been an active research of other drugs to fight alcoholism without having the "disulfiram-like adverse effect", i.e., without producing disagreeable reactions with alcohol.

Many anti-alcoholism agents have been proposed, among which there are the following: opioid antagonists, such as naltrexone, naloxone and nalmefene (cf. U.S. Pat. No. 4,882,335 and U.S. Pat. No. 5,086,058); acyl L-carnitine gamma-hydroxybutyrates (cf. EP 616,805-A1), gamma-hydroxybutyric acid salts (cf. U.S. Pat. No. 4,983,632) and gamma-hydroxybutyric acid amides (cf. WO 9806690-A1); 2-pyrimidinyl-1-piperazine derivatives such as ipsapirone (cf. U.S. Pat. No. 4,895,848); pyrrolidine derivatives (cf. U.S. Pat. No. 5,935,980); cholinesterase inhibitor, such as galanthamine (cf. U.S. Pat. No. 5,932,238); serotonin reuptake inhibitors, such as fluoxetine, and the combination of the later with opioid antagonists (cf. WO 9609047-A1).

Acamprosate calcium (cf. U.S. Pat. No. 4,355,043), of formula $(CH_3-CO-NH-CH_2-CH_2-CH_2-SO_3)_2Ca$, is one anti-alcoholism agent which is being used in practice. However, it has been mentioned that the use of this compound is far from being satisfactory, and that the evidence is not strong enough to support the introduction of this substance into routine clinical practice at present (cf. Moncrieff et al., "New drug treatments for alcohol problems: a critical appraisal", *Addiction* 1997, vol. 92, pp. 939–47; discussion in pp. 949–64). Thus, apparently none of the proposed treatments of alcoholism has proved to be completely satisfactory in practice, and the pharmacological fight against alcoholism is far from being solved.

DESCRIPTION OF THE INVENTION

According to an aspect of the present invention, it is provided a new compound of formula (I) or a physiologically-hydrolysable and acceptable amide of it, a stereoisomer or a mixture of stereoisomers of said compound (I) or of said amide, or a pharmaceutically acceptable salt or a pharmaceutically acceptable solvate thereof.

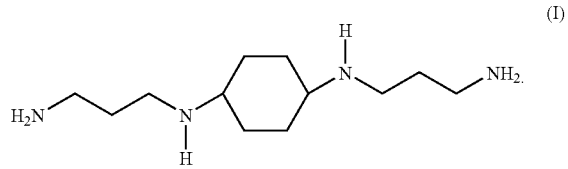

By the expression physiologically-hydrolysable and acceptable amide of (I) it is meant any amide of compound (I) in which one or several of its amine groups have formed amide groups with physiologically-acceptable acids, and in which said amide groups are hydrolysable under physiological conditions to yield acids which are themselves physiologically tolerable at dosages to be administered. The expression is thus to be understood as defining amides which are bioprecursor forms of compound of formula (I), i.e., pharmaceutically acceptable biologically degradable amides of the compound of formula (I) which, upon administration to a human being, are converted in the body to produce the compound of formula (I). Examples of such bioprecursors include amides of (I) with acetic acid, propionic acid, benzoic acid, methanesulfonic acid, benzenesulfonic acid and 4-methylbenzenesulfonic acid.

Compounds of the present invention can be in two different stereochemical forms, namely cis and trans in respect of the 1,4-substitution of the cyclohexane ring. The invention refers to both forms substantially pure, as well as to their mixtures.

In preferred embodiments of the present invention the compound is N,N'-bis(3-aminopropyl)cyclohexane-1,4-diamine, of formula (I), or a pharmaceutically acceptable salt or a pharmaceutically acceptable solvate thereof.

By pharmaceutically acceptable salt it is meant any addition salt with one or more physiologically tolerable acid at doses to be administered. Examples of these acids are inorganic acids such as HCl, HBr, HI, $HNO_3$, $H_2SO_4$, etc.; and organic acids such as acetic acid, benzoic acid, methanesulfonic acid, benzenesulfonic acid, 4-methylbenzenesulfonic acid, etc. In a preferred embodiment the pharmaceutically acceptable salt is the tetrametanesulfonate.

By pharmaceutically acceptable solvate it is meant any solvate with a solvent which is physiologically tolerable at doses to be administered, e.g. water. In a preferred embodiment, the compound of the present invention is N,N'-bis(3-aminopropyl)cyclohexane-1,4-diamine tetrametanesulfonate monohydrate, a compound here prepared for the first time, whose therapeutic activity is illustrated in the accompanying examples.

According to another aspect of the present invention, there is provided a preparation process of N,N'-bis(3-aminopropyl)cyclohexane-1,4-diamine, of formula (I), comprising the reduction of N,N'-bis(2-cyanoethyl)-cyclohexane-1,4-diamine of formula (II). In a preferred embodiment, this reduction is carried out by hydrogenation with Raney nickel catalyst.

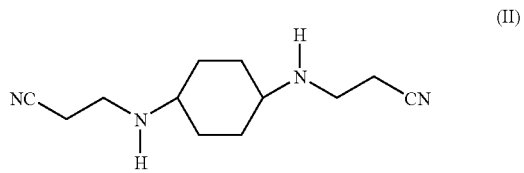

(II)

In a preferred embodiment of this preparation process, dinitrile (II) is prepared by reaction between 1,4-cyclohexanediamine and acrylonitrile ($CH_2$=CH—CN), the later two reactants being commercially available.

The above-mentioned reactions are carried out in conditions common in the art, illustrated in the accompanying examples. When 1,4-cyclohexanediamine is in a substantially pure stereochemcial form (cis or trans), the corresponding stereoisomers (cis or trans) of (II) and (I) are obtained. Preparation of salts of (I) (e.g. tetrametanesulfonate) is carried out by reaction with the corresponding acid (e.g. metanesulfonic acid) in a suitable solvent or mixture of solvents for precipitation of the salt.

The invention also relates to a method of therapeutic and/or prophylactic treatment of a patient suffering from alcoholism, comprising the administration of at least one of the compounds of the invention, together with pharmaceutically acceptable excipients or carriers. Thus, another aspect of the present invention is the use of the compounds of the invention for the preparation of a medicament for the therapeutic and/or prophylactic treatment of alcoholism in mammals, including human beings.

As illustrated in accompanying Examples, carried out with an animal model which is extrapolated to human beings, the compounds of the present invention cause a significant reduction in the alcohol consumption in mammals. The extent of this reduction depends on the dose and the duration of the treatment.

Pharmaceutical compositions of the anti-alcoholism compounds of the invention can be prepared in formulations suitable for oral or parental administration, according to the particular requirements of the application. Oral formulations are specially preferred. As well known by persons skilled in the art, the choice of excipients in the formulations depends not only on the chemical and physical characteristics of the active principle and the required posology, but also on the type of composition desired. Besides, the dosage of the active principle obviously varies in accordance with the body weight of the patient and his clinical condition. Typical doses are those between 1 and 100 mg of compound per kg, those between 20 mg/kg and 40 mg/kg being preferred.

An advantage of the present invention is that the anti-alcoholism activity of the compounds lasts for some time after the treatment period, what can allow a decrease in the dose, or even a total cure of the patient.

Another advantage of the present invention, in comparison with the unpleasant use of disulfiram, calcium cyanamide and other anti-alcoholism agents, is that the disulfiram-like adverse effect is virtually null. This probably indicates that the activity of the compounds of the present invention does not respond to a disulfiram-like mechanism of action.

The invention is illustrated by the following non-limiting examples.

EXAMPLES

Example 1

Preparation of N,N'-bis(2-cyanoethyl)-cyclohexane-1,4-diamine (II)

In a 5-liter reactor, 531.5 g of 1,4-cyclohexanediamine were placed and warmed at 80° C. until total fusion of the product. Then 675 mL of acrylonitrile were added and the mixture was warmed at 80° C. for 1 h, and at 100° C. for 2 h. Then 960 mL of ethanol were added and it was cooled down to room temperature, occurring the precipitation of a solid. After filtering, washing with ethanol and drying, 952.2 g (92.8%) of the title compound were obtained as a brown solid. Elemental analysis (%): theory, C 65.49, H 9.09, N 25.45; found, C 65.80, H 9.20, N 26.16.

Example 2

Preparation of N,N'-bis(3-aminopropyl)cyclohexane- 1,4-diamine (I)

A solution of 952.2 g of N,N'-bis(2-cyanoethyl)-cyclohexane-1,4-diamine (II) in 21.2 L of methanol was prepared and it was then saturated with ammonia. In a 50-liter hydrogenation reactor the solution was hydrogenated at 50° C. and a hydrogen pressure of 4 bar, for 40 h, with 200 g of Raney nickel catalyst. After filtering off the catalyst and distilling the solvent, 924.4 g (93.7%) of the title compound were obtained as a green oil. $^1$H-NMR spectrum (δ, ppm, $CDCl_3$): 1.05 (m, 4H), 1.48–1.66 (m, 10H), 1.92 (m, 4H), 2.35 (m, 2H), 2.65–2.79 (m, 8H). $^{13}$C-NMR spectrum (δ, ppm, $CDCl_3$): 31.8 (cyclohexane $CH_2$), 33.9 ($CH_2$), 40.1

($CH_2$—$NH_2$), 44.7 ($CH_2$—NH), 56.6 (cyclohexane CH). IR spectrum ($cm^{-1}$, KBr): 3272 ($NH_2$, NH), 2940 (aliphatic CH).

Example 3

Preparation of N,N'-bis(3-aminopropyl)cyclohexane-1,4-diamine tetramethanesulfonate monohydrate A solution of 350 mL of methanesulfonic acid in 1345 mL of ethyl acetate was added to a solution of 285.8 g of N,N'-bis(3-aminopropyl)cyclohexane-1,4-diamine (I) in 6880 mL of methanol. After stirring for 2 h, filtering, washing with ethanol and drying, 625 g of a crude solid were obtained. The solid was treated and stirred with water (5 mL per gram of solid) and activated charcoal for 2 h. After filtering off the charcoal, evaporating the water under vacuum, and drying at 40° C. until constant weight, 515 g (67.2%) of the title compound were obtained, with a melting point of 261-5° C. $^1$H-NMR spectrum ($\delta$, ppm, DMSO-$d_6$): 1.4 (m, 4H), 1.91 (m, 4H), 2.14 (m, 4H), 2.3 (s, 12H), 2.90 and 3.20 (m 10H), 8 (10 H). $^{13}$C-NMR spectrum ($\delta$, ppm, DMSO-$d_6$): 22.4 (cyclohexane $CH_2$), 24.6 ($CH_2$), 34.6 ($CH_2$—$NH_2$), 38.5 (acid $CH_3$), 38.6 (acid $CH_3$), 39.6 ($CH_2$—NH), 52.9 (cyclohexane CH). IR spectrum ($cm^{-1}$, KBr): 3440 ($H_2O$), 2944, 2860 (aliphatic CH), 1195 ($SO_3$). Elemental analysis (%): theory, C 30.48, H 7.30, N 8.88; found, C 30.79, H 7.04, N 8.88.

Example 4

Anti-alcoholism Activity of Compound (I) in Genetically-alcoholic Rats

As an animal model of alcoholic mammals, including human beings, adult Wistar rats of both sexes, belonging to the UChB strain were used. This strain of rats is the result of a long selection at the University of Chile, and rats belonging to it are known to be volunteer consumers of 10% (v/v) aqueous alcohol (cf. J. Mardones and N. Segovia-Riquelme, "Thirty two years of selection of rats by ethanol preference": UChA and UChB strains", *Neurobehav. Toxicol. and Teratol.* 1983, vol. 5, pp. 171–178). Thus, the rats used in these experiments can be considered genetically alcoholic.

Rats were kept in individual cages at 22° C., with alternative 12 h periods of light and darkness. Besides unlimited access to food, they had ad libitum access to water and 10% (v/v) aqueous alcohol. All experiments were double-blind, and results were analyzed using common statistical methods. As changes in alcohol consumption might be influenced by the eagerness of food and/or water intake, both the consumption of food and of water were measured and analyzed. However, experimental changes in the consumption of both food and water were not significant. In each experiment the following three periods of time were considered:

a) A reference period, consisting of the three days previous to treatment. The measured consumption values were used as reference for comparison purposes.

b) A treatment period, consisting of the three or six days during which aqueous solutions of the tested compound were intra-gastrically administered, always at the same time of the day. N,N'-bis(3-aminopropyl)cyclohexane-1,4-diamine tetramethanesulfonate monohydrate was administered at two doses, 20 mg/kg of body weight and 40 mg/kg, using aqueous solutions of the tested compound of concentrations 10 g/L and 20 g/L, respectively. Dose of 20 mg/kg was tested both for 3 consecutive days and 6 consecutive days. Dose of 40 mg/kg was tested only for 3 consecutive days.

c) A post-treatment period, consisting of the three days immediate after the treatment period, during which measurement were taken in order to establish the duration of the effect and the reversibility of the changes.

It was observed that treatment with 20 mg/kg for 6 days significantly ($p<0.01$) lowered alcohol consumption in a 25%, along the first 6 hours after administration. Treatment with 40 mg/kg for 3 days significantly lowered alcohol consumption in a 27%, and this decrease was kept along the post-treatment period. Decreases of alcohol consumption in the period of 6–24 h were smaller, what is associated with a reduction of concentration of active substance in blood.

Overall results indicate that N,N'-bis(3-aminopropyl)cyclohexane-1,4-diamine tetramethanesulfonate monohydrate has a substantial activity as anti-alcoholism agent. Its effect depend on treatment duration and dose.

Example 5

Anti-alcoholism Activity of Compound (I) During a Prolonged Treatment Period

The effect of the administration of N,N'-bis(3-aminopropyl)-cyclohexane-1,4-diamine tetramethanesulfonate monohydrate to Wistar rats of both sexes belonging to the UChB strain, at a dose of 40 mg/kg during a treatment period of 30 days, was assessed in an experiment analogous to the one of Example 4. Individual consumptions of alcohol and water, measured daily, were grouped in cycles of 3 consecutive days, thus reducing data to ten average values. Results showed a gradual decrease in alcohol consumption reaching a 71% decrease at the end of the treatment period. Water consumption showed a gradual increase, reaching more than 200%.

Example 6

Anti-alcoholism Activity of Compound (I) During a Post-treatment Period

The effect of the administration of N,N'-bis(3-aminopropyl)-cyclohexane-1,4-diamine tetramethanesulfonate monohydrate to Wistar rats of both sexes belonging to the UChB strain, during a post-treatment period of 27 days (9 cycles of 3 days) after the prolonged treatment of Example 5, was assessed in an analogous experiment. Results showed a gradual recovery in alcohol consumption, reaching a decrease of 24% at the end of the period. At the end of the post-treatment period, water consumption, which had reached more than 200% as a result of the prolonged treatment, decreased to 171% of the initial value. Therefore, the effect of N,N'-bis(3-aminopropyl)-cyclohexane-1,4-diamine tetramethanesulfonate monohydrate lasts substantially for a long time after a prolonged treatment, without recovering the initial levels of alcohol/water consumption.

Example 7

Assessment of Disulfiram-like Adverse Effect

The possible disulfiram-like adverse effect of N,N'-bis(3-aminopropyl)cyclohexane-1,4-diamine tetramethanesulfonate monohydrate was studied by gas-chromatographic measurements of the blood concentration of acetaldehyde in standard Wistar male rats, after the intraperitoneal administration of 2.76 g/kg of ethanol in the form of 10% (v/v) aqueous solution. Blood samples were taken from the tail (0.5, 1.0 and 2.0 h after ethanol administration) and from the suprahepatic vein (2.0 h after ethanol administration). It was observed that previous oral administration of the tested compound at a dose of 40 mg/kg (2, 6, 8 and 24 h before ethanol administration) did not raised levels of acetaldehyde in blood. It is then concluded that the tested compound does not block the metabolism of acetaldehyde significantly (contrary to what happens with disulfiram, as it was observed in a control test).

The invention claimed is:

1. A physiologically-hydrolysable and acceptable amide of the compound of formula (I), or a stereoisomer thereof, or a pharmaceutically acceptable salt or a pharmaceutically acceptable solvate of the compound of formula (I), or a stereoisomer thereof:

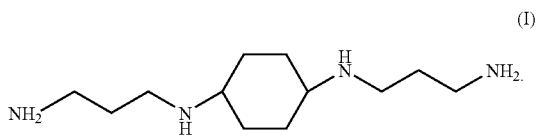

(I)

2. The compound according to claim 1, wherein said compound is a pharmaceutically acceptable salt or pharmaceutically acceptable solvate of N,N'-bis(3-aminopropyl)cyclohexane-1,4,-diamine, or a stereoisomer thereof.

3. The compound according to any of claims 1 or 2, wherein the pharmaceutically acceptable salt is a tetramethanesulfonate salt.

4. N,N'-bis(3-aminopropyl)cyclohexane-1,4-diamine tetrametanesulfonate monohydrate.

5. A process for preparing N,N'-bis(3-aminopropyl)cyclohexane-1,4-diamine comprising reducing N,N'-bis(2-cyanoethyl)-cyclohexane-1,4-diamine, of formula (II):

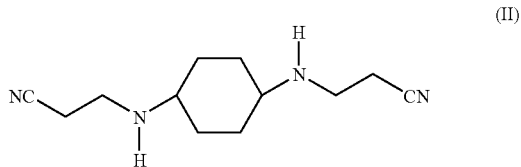

(II)

so as to obtain said N,N'-bis(3-aminopropyl)cyclohexane-1,4-diamine.

6. The process according to claim 5, wherein the reducing is carried out by hydrogenation with a Raney nickel catalyst.

7. The process according to any of claims 5 or 6, wherein the nitrile of formula (II) is prepared by reacting 1,4-cyclohexanediamine with acrylonitrile.

8. A composition comprising a compound of formula (I) or a physiologically-hydrolysable and acceptable amide thereof, a stereoisomer or a mixture of stereoisomers of said compound or of said amide, or a pharmaceutically acceptable salt or a pharmaceutically acceptable solvate thereof:

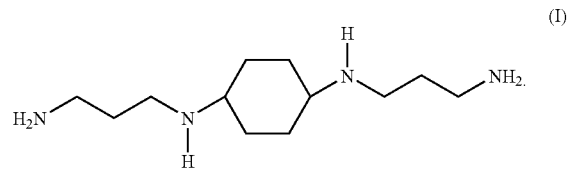

(I)

and, a pharmaceutically acceptable carrier.

9. A composition comprising the compound according to claim 3, as active substance, and a pharmaceutical acceptable carrier.

10. A method for therapeutic and/or prophylactic treatment of alcoholism in a mammal comprising administering, to a mammal in need of such treatment, an effective amount of a compound of formula (I) or a physiologically-hydrolysable and acceptable amide thereof, a stereoisomer or a mixture of stereoisomers of said compound or of said amide, or a pharmaceutically acceptable salt or a pharmaceutically acceptable solvate thereof:

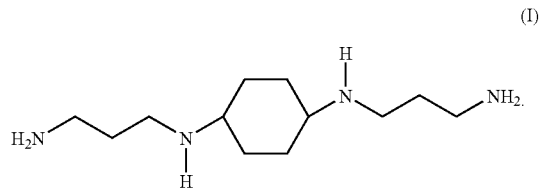

(I)

11. The method of claim 10, wherein said mammal is a human.

12. The method of claim 10, wherein said compound is N,N'-bis(3-aminopropyl)cyclohexane-1,4-diamine, a stereoisomer or a mixture of stereoisomers thereof, or a pharmaceutically acceptable salt or a pharmaceutically acceptable solvate thereof.

13. The method of claim 10, wherein the pharmaceutically acceptable salt is a tetramethanesulfonate salt.

14. The method of claim 10, wherein said compound is N,N'-bis(3-aminopropyl)cyclohexane-1,4-diamine tetrametanesulfonate monohydrate.

15. The composition of claim 8, wherein said compound is N,N'-bis(3-aminopropyl)cyclohexane-1,4-diamine, a stereoisomer or a mixture of stereoisomers thereof, or a pharmaceutically acceptable salt or a pharmaceutically acceptable solvate thereof.

16. The composition of claim 8, wherein the pharmaceutically acceptable salt is a tetramethanesulfonate salt.

17. The composition of claim 8, wherein said compound is N,N'-bis(3-aminopropyl)cyclohexane-1,4-diamine tetrametanesulfonate monohydrate.

* * * * *